United States Patent [19]

Naka et al.

[11] Patent Number: 5,401,764

[45] Date of Patent: Mar. 28, 1995

[54] BENZIMIDAZOLE DERIVATIVE COMPOSITIONS AND MEDICAL USE THEREOF

[75] Inventors: Takehiko Naka, Kobe; Kohei Nishikawa, Kyoto, all of Japan

[73] Assignee: Takeda Chemical Industries, Ltd., Osaka, Japan

[21] Appl. No.: 58,739

[22] Filed: May 10, 1993

Related U.S. Application Data

[62] Division of Ser. No. 997,703, Jan. 5, 1993, Pat. No. 5,328,919, which is a division of Ser. No. 687,238, Apr. 18, 1991, Pat. No. 5,196,444.

[30] Foreign Application Priority Data

| Apr. 27, 1990 | [JP] | Japan | 2-113148 |
| May 30, 1990 | [JP] | Japan | 2-141942 |
| Aug. 6, 1990 | [JP] | Japan | 2-208662 |
| Oct. 1, 1990 | [JP] | Japan | 2-264579 |
| Dec. 24, 1990 | [JP] | Japan | 2-413679 |

[51] Int. Cl.⁶ .................. C07D 403/1; A61K 31/415
[52] U.S. Cl. ..................................... 514/381; 548/253
[58] Field of Search ...................... 548/252; 514/381

[56] References Cited

U.S. PATENT DOCUMENTS

| 4,526,896 | 7/1985 | Schevrel et al. | 548/253 |
| 4,764,623 | 8/1988 | Kees | 548/253 |
| 4,775,679 | 6/1988 | Chang | 548/253 |
| 4,880,804 | 11/1989 | Carini et al. | 514/381 |

FOREIGN PATENT DOCUMENTS

| 28833 | 5/1981 | European Pat. Off. . |
| 28834 | 5/1981 | European Pat. Off. . |
| 245637 | 11/1987 | European Pat. Off. . |
| 253310 | 1/1988 | European Pat. Off. . |
| 0253310 | 1/1988 | European Pat. Off. . |
| 291969 | 11/1988 | European Pat. Off. . |
| 323841 | 7/1989 | European Pat. Off. . |
| 392317 | 10/1990 | European Pat. Off. . |
| 399732 | 11/1990 | European Pat. Off. . |
| 400835 | 12/1990 | European Pat. Off. . |
| 420237 | 4/1991 | European Pat. Off. . |

*Primary Examiner*—David B. Springer
*Attorney, Agent, or Firm*—Wegner, Cantor, Mueller & Player

[57] ABSTRACT

1-Acetoxyethyl 2-ethoxy-1-[[2'-(1H-tetrazol-5-yl)biphenyl-4-yl]methyl]benzimidazole-7-carboxylate or a pharmaceutically acceptable salt thereof has potent angiotensin II antagonistic activity and antihypertensive activity, thus being useful as therapeutic agents for treating circulatory system diseases such as hypertensive diseases, heart diseases (e.g. hypercardia, heart failure, cardiac infarction, etc.), strokes, cerebral apoplexy, nephritis, etc.

3 Claims, No Drawings

BENZIMIDAZOLE DERIVATIVE COMPOSITIONS AND MEDICAL USE THEREOF

This application is a division of Ser. No. 07/997,703, filed Jan. 5, 1993, now U.S. Pat. No. 5,328,919, which is a division of Ser. No. 07/687, 238, filed Apr. 18, 1991, now U.S. Pat. No. 5,196,444.

SUMMARY OF THE INVENTION

The present invention provides 1-acetoxyethyl 2-ethoxy-1-[[2'-(1H-tetrazol-5-yl)biphenyl-4-yl]methyl]-benzimidazole-7-carboxylate having potent anti-hypertensive activity and strong angiotensin II antagonistic action, which is of practical value in clinical use as therapeutic agents. The compound possesses highly angiotensin II receptor antagonistic activity as well as exerting strong oral and long-lasting angiotensin II antagonistic and anti-hypertensive action.

This compound is unexpectedly a potent angiotensin II antagonist which is of value in the treatment of circulatory system diseases such as hypertensive diseases, heart diseases, strokes, nephritis, etc.

Another aspect of the present invention relates to pharmaceutical compositions comprising an effective amount of 1-acetoxyethyl 2-ethoxy-1-[[2'-(1H-tetrazol-5-yl)biphenyl-4-yl]methyl]benzimidazole-7-carboxylate and a pharmaceutically acceptable carrier useful in treating circulatory system diseases such as hypertensive diseases, heart diseases, strokes, renal failure, nephritis, etc., and processes for preparing such compounds and compositions.

Still another aspect of the present invention relates to a method for treating said circulatory system diseases of animals, which comprises administering an effective amount of 1-acetoxyethyl 2-ethoxy-1-[[2'-(1H-tetrazol-5-yl)biphenyl-4-yl]methyl]benzimidazole-7-carboxylate or the pharmaceutical composition thereof to said animal.

DETAILED DESCRIPTION OF THE INVENTION

The present invention provides 1-acetoxyethyl 2-ethoxy-1-[[2'-(1H-tetrazol-5-yl)biphenyl4-yl]methyl]-benzimidazole-7-carboxylate and the pharmaceutically acceptable salts thereof, which possess strong angiotensin II antagonist activity and are of value in the treatment of circulatory diseases such as hypertensive diseases, heart diseases, strokes, cerebral diseases, nephritis, etc., pharmaceutical compositions comprising an effective amount of 1-acetoxyethyl 2-ethoxy-1-[[2'-(1H-tetrazol5-yl)biphenyl-4-yl]methyl]benzimidazole-7-carboxylate and a pharmaceutically acceptable carrier useful in treating said circulatory diseases, and processes for preparing such compounds and compositions.

Pharmaceutically acceptable salts of 1-acetoxyethyl 2-ethoxy-1-[[2'-(1H-tetrazol-5-yl)biphenyl-4-yl)methyl]benzimidazole-7-carboxylate can be formed as salts with non-toxic, physiologically or pharmaceutically acceptable acids or bases, for example salts with an inorganic acid such as hydrochloride, sulfate or nitrate, and, depending on compounds, salts with an organic acid such as acetate, oxalate, succinate or maleate, salts with an alkali metal such as sodium salt or potassium salt, or salts with an alkaline earth metal such as calcium salt.

1-acetoxyethyl 2-ethoxy-1-[[2'-(1H-tetrazol-5-yl)biphenyl-4-yl]methyl]benzimidazole-7-carboxylate and the salts thereof thus produced are less toxic, strongly inhibit the vasoconstrictive and hypertensive actions of angiotensin II, exert a hypotensive effect in animals, in particular mammals (e.g. human, dog, rabbit, rat, etc.), and therefore they are useful as therapeutics for not only hypertension but also circulatory diseases such as heart failure (hypertrophy of the heart, cardiac insufficiency, cardiac infarction or the like), strokes, cerebral apoplexy, nephropathy and nephritis. 1-acetoxyethyl 2-ethoxy-1-[[2'-(1H-tetrazol-5-yl)biphenyl-4-yl]methyl]benzimidazole-7-carboxylate and salts thereof according to the present invention strongly inhibit vasoconstriction and hypertension derived by angiotensin II and therefore possess potent anti-hypertensive activity in animals, more specifically mammal animals (e.g. humans, dogs, pigs, rabbits, rats, etc.). Further, 1-acetoxyethyl 2-ethoxy-1-[[2'-(1H-tetrazol-5-yl)biphenyl-4-yl]methyl]benzimidazole-7-carboxylate and salts thereof according to the present invention are of quite low toxicity and clinically useful in treating not only hypertension but also circulatory system diseases such as heart and brain diseases, strokes, renal failures, nephritis and the like.

For therapeutic use, 1-acetoxyethyl 2-ethoxy-1-[[2'-(1H-tetrazol-5-yl)biphenyl-4-yl]methyl]benzimidazole-7-carboxylate and salts thereof can be orally, parenterally, by inhalation spray, rectally, or topically administered as pharmaceutical compositions or formulations (e.g. powders, granules, tablets, pills, capsules, injections, syrups, emulsions, elixirs, suspensions, solutions and the like) comprising at least one such compound alone or in admixture with pharmaceutically acceptable carriers, adjuvants, vehicles, excipients and/or diluents. The pharmaceutical compositions can be formulated in accordance with conventional methods. The term parenteral as used herein includes subcutaneous injections, intravenous, intramuscular, intraperitoneal injections, or infusion techniques. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a non-toxic parenterally acceptable diluent or solvent, for example, as a solution in water. Among the acceptable vehicles or solvents that may be employed are water, Ringer's solution, and isotonic sodium chloride solution. In addition, sterile, fixed oils are conventionally employed as a solvent or suspending medium. For this purpose any bland fixed oil or fatty acid may be employed including natural, synthetic, or semi-synthetic fatty oils or acids, and natural, synthetic, or semi-synthetic mono-, di-, or triglycerides.

Suppositories for rectal administration of the drug can be prepared by mixing the drug with a suitable non-irritating excipient such as cocoa butter and polyethylene glycols which are solid at ordinary temperatures but liquid at the rectal temperature and will therefore melt in the rectum and release the drug. Solid dosage forms for oral administration may include powders, granules, tablets, pills, and capsules as mentioned above. In such solid dosage forms, the active compound may be admixed with at least one additive such as sucrose, lactose, celluloses, mannitol, maltitol, dextran, starches, agars, alginates, chitins, chitosans, pectins, tragacanth gums, arabic gums, gelatins, collagens, casein, albumin, and synthetic or semi-synthetic polymers or glycerides. Such dosage forms may also comprise, as is normal practice, additional substances other than inert diluents, e.g., lubricating agents as magnesium stearate, preservatives such as parabens and sorbic acid, antioxidants such as ascorbic acid, α-tocopherol and cysteine, disintegrants, binders, thickening, buffering, sweetening, flavoring, and perfuming agents. Tablets and pills can additionally be prepared with enteric coatings. Liquid dosage forms for oral administration may include pharmaceutically acceptable emulsions, syrups, elixirs, suspensions, solutions containing inert diluents commonly used in the art, such as water.

Specific dose levels for any particular patient will be employed depending upon a variety of factors including the activity of specific compounds employed, the age, body weight, general health, sex, diet, time of administration, route of administration, rate of excretion, drug combination, and the severity of the particular disease undergoing therapy. The dose varies with the diseases to be treated, symptoms, subjects and administration routes, and it is desirable that a daily dose of 1 to 50 mg for oral administration or 1 to 30 mg for intravenous injection is divided into 2 to 3 administrations when used as an agent for the therapy in adults. For example, when used for treating adult essential hypertension, the active ingredient will preferably be administered in an appropriate amount, for example, about 10 mg to 100 mg a day orally and about 5 mg to 50 mg a day intravenously. The active ingredient will preferably be administered in equal doses two or three times a day.

The foregoing is merely illustrative of the invention and is not intended to limit the invention to the disclosed compounds.

EXAMPLES

By the following working examples, experimental examples and reference examples, the present invention will be explained more concretely, but they should not be interpreted as limiting the invention in any manner.

Examples of abbreviations in this specification are as follows:

Me: methyl, Et: ethyl, Tet: tetrazolyl, cycl: cyclo-, Pr: propyl, Bu: butyl, Pen: pentyl, Bu: butyl, Hex: hexyl, Hep: heptyl, Ph: phenyl, DMF: dimethylformamide, and THF: tetrahydrofuran.

REFERENCE EXAMPLE 1

Ethyl 2-carboxy-3-nitrobenzoate

A mixture of 3-nitrophthalic acid (35 g) in ethanol (300 ml) containing conc. sulfuric acid (20 ml) was heated under reflux for 24 hours. The solvent was evaporated in vacuo and the residue was poured into cold water (700 ml). The mixture was extracted with ethyl acetate. The organic layer was washed with water and shaken with an aqueous solution of potassium carbonate. The aqueous layer was made acidic with hydrochloric acid and the mixture was extracted with methylene chloride. The organic layer was washed with water, then dried, followed by evaporation of the solvent. The resultant solid (29 g, 74%) was used for the subsequent reaction without purification.

$^1$H-NMR(90 MHz, CDCl$_3$) δ: 1.43(3H,t), 4.47(2H,q), 7.70(1H,t), 8.40(2H,d), 9.87(1H,br s)

IR(Nujol) cm$^{-1}$: 1725, 1535, 1350, 1300, 1270

REFERENCE EXAMPLE 2

Ethyl 2-t-butoxycarbonylamino-3-nitrobenzoate

A mixture of ethyl 2-carboxy-3-nitrobenzoate (23.9 g) and thionyl chloride (12 ml) in benzene (150 ml) were heated under reflux for 3 hours. The reaction mixture was concentrated to dryness. The resultant acid chloride (26 g, quantitative) was dissolved in methylene chloride (20 ml). The solution was added dropwise to a mixture of sodium azide (9.75 g) in dimethylformamide(DMF) (20 ml) with stirring vigorously. The reaction mixture was poured into a mixture of ether-hexane (3:1, 200 ml) and water (250 ml) to separate into two layers. The organic layer was washed with water, then dried, followed by evaporation of the solvent. The residue was dissolved in t-butanol (200 ml) and the solution was heated gradually with stirring, followed by heating under reflux for 2 hours. The reaction mixture was concentrated in vacuo to give an oily product (30 g).

$^1$H-NMR(90 MHz, CDCl$_3$) δ: 1.40(3H,t), 1.53(9H,s), 4.43(2H,q), 7.23(1H,t), 8.03–8.27(2H,m), 9.70(1H,br s)

IR(Neat) cm$^{-1}$: 3320, 2980, 1740, 1585, 1535, 1500, 1440, 1375, 1265, 1155

WORKING EXAMPLE 1

Ethyl 2-[[2'-cyanobiphenyl)]amino]-3-nitrobenzoate

To a solution of ethyl 2-t-butoxycarbonylamino-3-nitrobenzoate (20 g) in tetrahydrofuran (50 ml) was added, while stirring under ice-cooling, sodium hydride (60% dispersion in mineral oil, 2.8 g). The mixture was stirred at room temperature for 20 minutes and to the mixture were then added 4-(2-cyanophenyl)benzyl bromide (18 g) and potassium iodide (360 mg), followed by heating for 10 hours under reflux. The solvent was evaporated to dryness and the residue was partitioned between water (250 ml) and ether (200 ml). The organic layer was washed with water, dried and concentrated to give a yellow syrup. The syrup was dissolved in a mixture of trifluoroacetic acid (60 ml) and methylene chloride (40 ml) and the solution was stirred for one hour at room temperature. The reaction mixture was concentrated to dryness and to the residue was added ethyl ether (200 ml) to give crystals. The crystals were collected by filtration, washed with ether to give pale yellow crystals (22.1 g, 85%), m.p. 118°–119° C.

$^1$H-NMR(90MHz,CDCl$_3$) δ: 1.37(3H,t), 4.23(2H,s), 4.37(2H,q), 6.37(1H,t), 7.33–7.83(9H,m), 7.97–8.20(2H,m)

IR(Nujol)cm$^{-1}$: 3280, 2220, 1690, 1575, 1530, 1480, 1450, 1255, 1105, 755

WORKING EXAMPLE 2

Ethyl 3-amino-2-[[2'-cyanobiphenyl-4-yl)methyl]amino]benzoate

To a solution of ethyl 2-[[(2'-cyanobiphenyl-4-yl)methyl]amino]nitrobenzoate (10.4 g) in ethanol (50 ml) was added stannous dichloride dihydrate (28.1 g) and the mixture was stirred at 80° C. for two hours. The solvent was evaporated to dryness. To the ice-cooling mixture of the residue in ethyl acetate (300 ml) was added dropwise 2N NaOH (500 ml) with stirring. The aqueous layer was extracted with ethyl acetate (200 ml×2). The organic layers were combined, washed with water, and dried. The solvent was evaporated to dryness and the residue was purified by column chromatography on silica gel to give crystals. Recrystallization from ethyl acetate—hexane gave colorless crystals (7.3 g, 79%), m.p. 104°–105° C.

$^1$H-NMR(200 MHz, CDCl$_3$) δ: 1.33(3H,t), 4.23(2H,s), 4.27(2H,q), 6.83–6.93(2H,m), 7.35–7.55(7H,m), 7.64(1H,dt), 7.76(dd)

IR(KBr) cm$^{-1}$: 3445, 3350, 2220, 1680, 1470, 1280, 1240, 1185, 1160, 1070, 1050, 1020, 805, 750

WORKING EXAMPLE 3

Ethyl 1-[(2'-cyanobiphenyl-4-yl)methyl]-2-ethoxybenzimidazole-7-carboxylate

Acetic acid (0.2 g) was added to a solution of ethyl 3-amino-2-N-[2'-cyanobiphenyl-4-yl)methyl]aminobenzoate (1.0 g) in ethyl orthocarbonate (5 ml). The mixture was stirred at 80° C. for one hour. The reaction mixture was concentrated, and the concentrate was dissolved in ethyl acetate. The solution was washed with an aqueous solution of sodium hydrogen carbonate and water. The solvent was evaporated to give crystals. Recrystallization from ethyl acetate—benzene afforded colorless crystals (0.79 g, 69%), m.p.131°–132° C.

| Elemental Analysis for C$_{26}$H$_{23}$N$_3$O$_3$: | | | |
|---|---|---|---|
| | C(%) | H(%) | N(%) |
| Calcd.: | 73.39; | 5.45; | 29.88 |
| Found: | 73.36; | 5.42 | 9.83 |

$^1$H-NMR(200 MHz, CDCl$_3$) δ: 1.24(3H,t), 1.49(3H,t), 4.24(2H,q), 4.68(2H,q), 5.72(2H,s), 7.10(2H,d), 7.19(1H,t), 7.38–7.46(4H,m), 7.56–7.66(2H,m), 7.73–7.77(2H,m)

IR(KBr) cm$^{-1}$: 2220, 1720, 1550, 1480, 1430, 1280, 1245, 1215, 1040, 760, 740

WORKING EXAMPLE 4

Ethyl 2-ethoxy-1-[[2'-(1H-tetrazol-5-yl)biphenyl-4-yl]methyl]-benzimidazole-7-carboxylate A mixture of ethyl 1-[(2'-cyanobiphenyl-4-yl)methyl]-2-ethoxybenzimidazole-7-carboxylate (0.7 g) and trimethyltin azide (0.7 g) in toluene (15 ml) was heated under reflux for 4 days. The reaction mixture was concentrated to dryness and to the residue were added methanol (20 ml) and 1N-HCl (10 ml). The mixture was stirred at room temperature for 30 minutes and adjusted to pH 3 to 4 with 1N NaOH. After removal of the solvent, the residue was partitioned between chloroform and water. The organic layer was washed with water and dried, and the solvent was evaporated to dryness to give a syrup. The syrup was purified by column chromatography on silica gel to give crystals. Recrystallization from ethyl acetate—benzene afforded colorless crystals (0.35 g, 45%), m.p. 158°–159° C.

| Elemental Analysis for C$_{26}$H$_{24}$N$_6$O$_3$: | | | |
|---|---|---|---|
| | C(%) | H(%) | N(%) |
| Calcd.: | 66.65; | 5.16; | 17.94 |
| Found: | 66.61; | 5.05; | 17.84 |

$^1$H-NMR(200 MHz,CDCl$_3$) δ: 1.09(3H,t), 1.43(3H,t), 4.02(2H,q), 4.30(2H,q), 5.57(2H,s), 6.71(2H,d), 6.83–6.96(4H,m), 7.27–7.31(1H,m), 7.40(1H,dd), 7.55–7.66(2H,m), 8.04–8.09(1H,m)

IR(KBr) cm$^{-1}$: 1720, 1605, 1540, 1470, 1430, 1250, 1040, 750

WORKING EXAMPLE 5

2-Ethoxy-1-[[2'-(1H-tetrazol-5-yl)biphenyl-4-yl]methyl]benzimidazole-7-carboxylic acid A solution of ethyl 2-ethoxy-1-[[2'-(1H-tetrazol-5-yl)biphenyl-4-yl]methyl]benzimidazole-7-carboxylate (0.24 g) and 1N NaOH (1.5 ml) in ethanol (4 ml) was stirred at 80° C. for one hour. The reaction mixture was concentrated, and the concentrate was extracted with water and ethyl acetate. The aqueous layer was adjusted to pH 3–4 with 1N-HCl to give crystals. Recrystallization of the crystals from ethyl acetate—methanol afforded colorless crystals (0.15 g, 67%), m.p. 183°–185° C.

| Elemental Analysis for C$_{24}$H$_{20}$N$_6$O$_3$.1/5H$_2$O: | | | |
|---|---|---|---|
| | C(%) | H(%) | N(%) |
| Calcd.: | 64.91; | 4.63; | 18.93 |
| Found: | 65.04; | 4.51; | 18.77 |

$^1$H-NMR(200 MHz,DMSO-d$_6$) δ: 1.38(3H,t), 4.58(2H,q), 5.63(2H,s), 6.97(4H,q), 7.17(1H,t), 7.47–7.68(6H,m)

IR(KBr) cm$^{-1}$: 1710, 1550, 1480, 1430, 1280, 1240, 1040, 760

WORKING EXAMPLE 6

2-Ethoxy-1-[[2'-(N-triphenylmethyltetrazol-5-yl)biphenyl-4-yl]methyl]benzimidazole-7-carboxylic acid To a solution of 2-ethoxy-[[2'-(1H-tetrazol-5-yl)biphenyl-4-yl]methyl]benzimidazole-7-carboxylic acid (2.07 g) in methylene chloride (10 ml) were added trityl chloride (1.59 g) and triethylamine (0.8 ml). The mixture was stirred at room temperature for one hour. The reaction mixture was washed with water, dried and concentrated to dryness. The residue was purified by column chromatography on silica gel to give crystals. Recrystallization of crude crystals thus obtained from ethyl acetate—benzene gave colorless crystals (2.12 g, 66%), m.p. 168°–170° C.

| Elemental Analysis for C$_{43}$H$_{34}$N$_6$O$_3$: | | | |
|---|---|---|---|
| | C(%) | H(%) | N(%) |
| Calcd.: | 75.64; | 5.02; | 12.31 |
| Found: | 75.37; | 4.96; | 12.20 |

$^1$H-NMR(200 MHz,CDCl$_3$) δ: 1.40(3H,t), 4.61(2H,q), 5.58(2H,s), 6.76(2H,d), 6.91–6.96(8H,m), 7.12(1H,t), 7.17–7.41(12H,m), 7.60(1H,dd), 7.73–7.82(2H,m)

WORKING EXAMPLE 7

Pivaloyloxymethyl 2-ethoxy-1-[[2'-(1H-tetrazol-5-yl)biphenyl-4-yl]benzimidazole-7-carboxylate To a solution of 2-ethoxy-1-[[2'-(N-triphenylmethyltetrazol-5-yl)biphenyl-4-yl]methyl]benzimidazole-7-carboxylic acid (2.2 g) in DMF (10 ml) were added potassium carbonate (0.53 g) and pivaloyloxymethyl iodide (0.94 g), and the mixture was stirred for 30 minutes at room temperature. To the reaction mixture was added water and the mixture was extracted with ethyl acetate. The organic layer was washed with water and dried. After removal of the solvent, the residue was dissolved in methanol (30 ml) and 1N-HCl (6 ml). The mixture was stirred for one hour at room temperature. The reaction mixture was concentrated to dryness and the residue was partitioned between water and ethyl acetate. The organic layer was washed with water and dried. After removal of the solvent, the residue was purified by column chromatography on silica gel to give crystals. The crystals were recrystallized from ethyl acetate—hexane to give colorless crystals (1.13 g, 63%), m.p. 104°–106° C.

| Elemental Analysis for $C_{30}H_{30}N_6O_5.1/5C_4H_8O_2.1/5C_6H_{14}$: | | | |
|---|---|---|---|
| | C(%) | H(%) | N(%) |
| Calcd.: | 65.06; | 5.90; | 14.32 |
| Found: | 64.79; | 5.85; | 14.43 |

$^1$H-NMR(200 MHz,CDCl$_3$) δ: 1.13(9H,s), 1.44(3H,t), 4.37(2H,q), 5.61(2H,s), 5.68(2H,s), 6.80(2H,d), 6.93(2H,d), 6.99–7.11(2H,m), 7.33–7.37(1H,m), 7.49–7.54(1H,m), 7.59–7.62(2H,m), 8.03–8.07(1H,m)

WORKING EXAMPLE 8

1-(Cyclohexyloxycarbonyloxy)ethyl 2-ethoxy-1-[[2'-(1H-tetrazol-5-yl)biphenyl-4-yl]methyl]-benzimidazole-7-carboxylate To a solution of 2-ethoxy-1-[[2'-(N-triphenylmethyltetrazol-5-yl)biphenyl-4-yl]methyl]benzimidazole-7-carboxylic acid (0.5 g) in DMF (5 ml) were added potassium carbonate (0.12 g) and cyclohexyl 1-iodoethyl carbonate (0.26 g). The mixture was stirred for one hour at room temperature. To the reaction mixture was added water and the mixture was extracted with ethyl acetate. The organic layer was washed with water and dried. After removal of the solvent, the residue was dissolved in methanol (10 ml) and to the solution was added 1N-HCl (2 ml). The mixture was stirred for one hour at room temperature. The reaction mixture was concentrated to dryness and the residue was partitioned between ethyl acetate and water. The organic layer was washed with water and dried. After removal of the solvent, the residue was purified by column chromatography on silica gel to give colorless powder (0.21 g, 47%), m.p. 103°–106° C.

| Elemental Analysis for $C_{33}N_{34}N_6O_6$: | | | |
|---|---|---|---|
| | C(%) | H(%) | N(%) |
| Calcd: | 64.91; | 5.61; | 13.76 |
| Found: | 64.94; | 5.71; | 13.66 |

To the powder (1 g) obtained as above was added ethanol (6 ml). The mixture was stirred for 3 hours at room temperature and allowed to stand under ice-cooling. The mixture was then stirred for one hour at temperatures not higher than 10° C. Resultant crystals were collected by filtration and washed with cold ethanol. The crystals were dried at 25° C. for 9 hours under reduced pressure, then at 35° C. for further 18 hours to obtain white powdery crystals (0.94 g), m.p. 158°–166° C. (decomp.).

| Elemental Analysis for $C_{33}H_{34}N_6O_6$: | | | |
|---|---|---|---|
| | C(%) | H(%) | N(%) |
| Calcd.: | 64.91; | 5.61; | 13.76 |
| Found: | 64.73; | 5.66; | 13.64 |

$^1$H-NMR (200 MHz) δ: 1.13–1.84(16H,m), 4.28–4.55(3H,m), 5.65(2H,d), 6.72(1H,q), 6.81(2H,d), 6.93(2H,d), 7.03(1H,t), 7.22–7.23(1H,m), 7.31–7.36(1H,m), 7.52–7.60(3H,m), 8.02–8.07(1H,m)

IR(KBr) cm$^{-1}$: 2942, 1754, 1717, 1549, 1476, 1431, 1076, 1034, 750

MS(m/z): 611 [M+H]$^+$ In substantially the same manner as Working Example 8, the following compound (Working Example 9) was synthesized.

WORKING EXAMPLE 9

1-Acetoxyethyl 2-ethoxy-1-[[2'-(1H-tetrazol-5-yl)biphenyl-4-yl]methyl]benzimidazole-7-carboxylate Yield: 3]%, m.p.: 105°–107° C.

| Elemental Analysis for $C_{28}H_{26}N_6O_5.0.5H_2O$: | | | |
|---|---|---|---|
| | C(%) | H(%) | N(%) |
| Calcd.: | 62.80; | 5.08; | 15.69 |
| Found: | 62.77; | 4.69; | 15.85 |

$^1$H-NMR(200 MHz,CDCl$_3$) δ: 1.46(3H,t), 1.49(3H,d), 4.47–4.62(2H,m), 5.59(1H,d), 5.83(1H,d), 6.84(1H,q), 6.90(2H,d), 7.03(2H,d), 7.11(1H,t), 7.34–7.39(1H,m), 7.49(1H,d), 7.53–7.61(3H,m), 8.07–8.11(1H,m)

EXPERIMENTAL EXAMPLE 1

Inhibition of binding of angiotensin II to angiotensin receptor

[Method]

An experiment of inhibition on the binding of angiotensin II (A II) to A II receptor was conducted by modifying the method of Douglas et al. [Endocrinology, 102, 685–696 (1978)]. An A II receptor membrane fraction was prepared from bovine adrenal cortex.

The compound of the present invention (10$^{-6}$M or 10$^{-7}$M) and $^{125}$I-angiotensin II ($^{125}$I-A II) (1.85 kBq/50 μl) were added to the receptor membrane fraction, and the mixture was incubated at room temperature for one hour. The receptor-bound and free $^{125}$I-A II were separated through a filter (Whatman GF/B filter), and the radioactivity of $^{125}$I-A II bound to the receptor was measured.

[Results]

The results relating to the compounds of the present invention are shown in Table 1.

EXPERIMENTAL EXAMPLE 2

Inhibitory effect of the compound of the present invention on pressor action of A II

[Method]

Jcl: SD rats (9 week old, male) were employed. On the previous day of the experiment, these animals were applied with cannulation into the femoral artery and vein under anesthesia with pentobarbital Na. The animals were fasted but allowed to access freely to drinking water until the experiment was started. Just on the day of conducting the experiment, the artery cannula was connected with a blood-pressure transducer, and the average blood pressure was recorded by means of polygraph. Before administration of the drug, the pressor action due to intravenous administration of A II (100 ng/kg) as the control was measured. The drugs were orally administered, then, at each point of the measurement, A II was administered intravenously, and the pressor action was similarly measured. By comparing the pressor action before and after administration of the drug, the percent inhibition by the drug on A II-induced pressor action was evaluated.

[Results]

The results relating to the compounds of the present invention are shown in Table 1.

TABLE 1

| Working Example | Radioreceptor Assay | | Pressor Response to |
| | $1 \times 10^{-7}$M | $1 \times 10^{-6}$M | AII (3 mg/kg, p.o) |
| --- | --- | --- | --- |
| 9 | 63 | 91 | +++ a) | a): +++ ≧ 70% > ++ ≧ 50% ≧ + > 30% > −

The foregoing is merely illustrative of the invention and is not intended as limiting the scope of the invention which is defined by the following claims:

What is claimed is:

1. 1-Acetoxyethyl 2-ethoxy-1-[[2'-(1H-tetrazol-5-yl)biphenyl-4-yl]methyl]benzimidazole-7-carboxylate or a pharmaceutically acceptable salt thereof.

2. A pharmaceutical composition for antagonizing angiotensin II which comprises a therapeutically effective amount of 1-acetoxyethyl 2-ethoxy-1-[[2'-(1H-tetrazol-5-yl)biphenyl-4-yl]methyl]benzimidazole-7-carboxylate or a pharmaceutically acceptable salt thereof in admixture with a pharmaceutically acceptable carrier, excipient or diluent.

3. A method for antagonizing angiotensin II in a mammal which comprises administering to a mammal in need thereof a therapeutically effective amount of 1-acetoxyethyl 2-ethoxy-1-[[2'-(1H-tetrazol-5-yl)biphenyl-4-yl]methyl]benzimidazole-7-carboxylate or a pharmaceutically acceptable salt thereof.

* * * * *